United States Patent [19]

Dougherty et al.

[11] Patent Number: 4,755,519
[45] Date of Patent: Jul. 5, 1988

[54] METHODS OF TREATING AND PREVENTING TALL FESCUE TOXICOSIS BY THE ADMINISTRATION OF THIAMIN

[75] Inventors: Charles T. Dougherty; Nelson Gay, both of Lexington, Ky.

[73] Assignee: University of Kentucky Research Foundation, Lexington, Ky.

[21] Appl. No.: 866,211

[22] Filed: May 22, 1986

[51] Int. Cl.$^4$ ............................................. A61K 31/51
[52] U.S. Cl. ..................................................... 514/276
[58] Field of Search ......................................... 514/276

[56] References Cited

U.S. PATENT DOCUMENTS 4,087,556  5/1978  Harte ..................................... 426/2

OTHER PUBLICATIONS

Edwin & Jackman, Ruminant Thiamine Requirement in Perspective, (1981/1982), pp. 237–250.
Brent & Bartley, Thiamin and Niacin in the Rumen, (1984), pp. 813–822.
Hooper, Pyrrolizidine Alkaloid Poisoning—Pathology with Particular Reference to Differences in Animal and Plant Species, pp. 161–177.

Primary Examiner—Albert T. Meyers
Assistant Examiner—John M. Kilcoyne
Attorney, Agent, or Firm—King and Schickli

[57] ABSTRACT

A method of treating and effectively alleviating the symptoms of tall fescue toxicosis in domestic farm animals includes the administering of thiamin at therapeutic levels into the feed for the animals. A method of preventing tall fescue toxicosis in animals grazing or feeding on endophyte infected tall fescue is also provided.

4 Claims, No Drawings

4,755,519

METHODS OF TREATING AND PREVENTING TALL FESCUE TOXICOSIS BY THE ADMINISTRATION OF THIAMIN

TECHNICAL FIELD

The present invention relates to the animal husbandry field and more particularly, to a method of treating tall fescue toxicosis in domestic farm animals.

BACKGROUND OF THE INVENTION

Approximately 45 million acres of grassland are occupied by tall fescue in the continental United States alone. These grasslands are primarily used to support beef cow herds for the production and sale of cull beef, feeder and stocker calves and herd replacements. Most of the tall fescue grasslands are severely infested with an endophyte fungus, Acremonium coenophialum, which is responsible for a syndrome commonly known as tall fescue toxicosis.

Endophyte infected tall fescue plants produce and contain pyrrolizidine alkaloids. Pyrrolizidine alkaloids cause three main toxic effects in domestic farm animals such as horses, cattle and sheep. The alkaloids exert their effects on tissue by causing necrosis, by inhibiting mitosis and thereby causing megalocytosis and/or by acting directly on blood vessels and causing edema and vascular disease. Typical symptoms include, for example, hepatic lesions of the liver and intestitial pneumonia in the lungs (*Effects of Poisonous Plants on Livestock*, by Richard F. Keeler, Kent R. Van Kampen & Lynn F. James, Academic Press, 1978).

Tall fescue toxicosis severely limits the productivity of as many as twelve million cattle in terms of conception, milk production and live weight gain. Approximately ten million feeder calves and stocker cattle also suffer from tall fescue toxicosis each year. Consequently, cattle from tall fescue areas, principally Kentucky, Tennessee, Missouri, Virginia and southern Ohio, Indiana and Illinois, are discounted by stocker and finishing operations.

All together, tall fescue toxicosis in cattle and sheep cause losses in animal productivity estimated in the hundreds of millions of U.S. dollars annually. A need, therefore exists, for a method of effectively treating tall fescue toxicosis in domestic farm animals.

During our studies of the tall fescue toxicosis problem, we have determined that the pyrrolizidine alkaloids of the endophyte infected tall fescue grasses are chemically similar to and may function as cosubstrates for the thiaminase mediated destruction of thiamin. As such, we hypothesize that tall fescue toxicosis may be a form of thiamin deficiency.

In testing this hypothesis, we have discovered that cattle suffering from tall fescue toxicosis may effectively be treated with feed supplemented with thiamin.

Thiamin is a naturally occuring substance involved as a cofactor in many enzyme systems of plant and animal cells. Thiamin is chemically synthesized in large amounts and widely used as a nutritional supplement for monogastric animals such as man, and chickens. Thiamin has also been advocated as a means of alleviating stress such as shipping fever and has been studied extensively in feedlot systems. Thiamin is, however, not generally used in ruminant nutrition for it is generally considered as unnecessary. This is because ruminants such as cattle include organisms capable of synthesizing sufficient amounts of thiamin for use by the animal within their rumen.

Thiamin has also been proposed as a method of treating polioencephalomalacia or PEM. We, however, believe we are the first to propose and demonstrate that thiamin may be used to effectively treat tall fescue toxicosis.

SUMMARY OF THE INVENTION

Accordingly, it is a primary object of the present invention to provide a simple method for effectively treating the adverse effects of tall fescue toxicosis on domestic farm animals.

It is another object of the present invention to provide a method of treating domestic farm animals suffering from tall fescue toxicosis with a supplemented diet to promote more rapid weight gain and improved recovery from the ailment.

Still another object of the invention is to provide a method of effectively treating ruminants with tall fescue toxicosis through the administration of a therapeutic dosage of thiamin.

A further object of the present invention is to allow the utilization of endophyte infected tall fescue as hay or haylage without the animals experiencing the adverse effects of tall fescue toxicosis.

Additional objects, advantages and other novel features of the invention will be set forth in part in the description that follows and in part will become apparent to those skilled in the art upon examination of the following or may be learned with the practice of the invention. The objects and advantages of the invention may be realized and attained by means of the instrumentalities and combinations particularly pointed out in the appended claims.

To achieve the foregoing and other objects, and in accordance with the purposes of the present invention as described herein, a method is provided for treating and substantially alleviating the symptoms of tall fescue toxicosis in domestic farm animals such as horses, cattle and sheep. The method comprises the administration of thiamin at therapeutic levels to the animals suffering from tall fescue toxicosis.

More specifically, the method includes the steps of introducing thiamin at therapeutic levels into the feed of the animals. This thiamin containing feed may then be fed to the animals in accordance with normal dry lot feeding procedures known in the art.

Preferably, the thiamin is in the form of thiamin nitrate. Thiamin nitrate is particularly stable and well adapted for supplementation into feed stock.

In accordance with the more specific aspects of the present invention, the thiamin is administered to the animals suffering from tall fescue toxicosis at a rate between 0.5 and 1.0 grams per animal per day for steers and heifers in the 500–800 lbs. liveweight range and to other animals at a similar rate adjusted for liveweight. Thus, the thiamin is administered in a dosage of approximately 0.000625 to 0.002 g/lbs of the animal. The treatment program continues at this rate for approximately 60 days at which time the animals have substantially recovered from the adverse effects of the tall fescue toxicosis.

Since endophyte infected tall fescue grasses exhibit certain natural selection characteristics including increased growth rates and improved insect resistance, it is apparent that the tall fescue toxicosis problem will continue to increase. Advantageously, the present invention provides a method for treating the symptoms of tall fescue toxicosis in farm animals and substantially eliminates the adverse and costly effects on animal productivity resulting from the ailment.

In accordance with yet another aspect of the present invention, a method is provided for preventing the symptoms of tall fescue toxicosis in animals grazing in endophyte infected tall fescue fields. This method includes the step of supplementing thiamin at therapeutic levels into the animal's diet. For example, the thiamin may be added to the mineral supplements such as mineral licks or salt blocks left in the field for cattle.

Preferably, the thiamin is introduced into the mineral supplement at such a level as to provide the animal with approximately 0.000625 to 0.002 grams of thiamin per pound of the animal per day. The prophylactic use of the thiamin continues throughout the entire time the animals are grazing in the endophyte infected tall fescue field. With such a treatment, cattle coming off infected fescue fields are not suffering from tall fescue toxicosis and, therefore, are no longer the subject of discounting by brokers.

Still other objects of the present invention will become readily apparent to those skilled in this art from the following description wherein there is shown and described a preferred embodiment of this invention, simply by way of illustration of one of the modes best suited to carry out the invention. As it will be realized, the invention is capable of other different embodiments, and its several details are capable of modifications in various, obvious aspects all without departing from the invention. Accordingly, the descriptions will be regarded as illustrative in nature and not as restrictive.

DETAILED DESCRIPTION OF THE INVENTION

As pointed out above, the present invention is concerned with a method of treating and substantially alleviating the symptoms of tall fescue toxicosis in domestic farm animals such as horses, cattle and sheep. The present invention rests on the discovery that a thiamin supplemented diet effectively relieves certain symptoms of tall fescue toxicosis and, for example, promotes more rapid weight gain in cattle that have previously been grazing in endophyte infected tall fescue fields.

In accordance with the teachings of the present invention, cattle are brought in off tall fescue grazing areas or ranges and maintained in dry lot prior to sale or slaughter. Once in dry lot, cattle are fed ground corn and/or corn silage supplemented with thiamin at therapeutic levels. For stability, the thiamin may be in the form of thiamin nitrate but, of course, other sources of thiamin such as thiamin hydrochloride may be used.

The thiamin is introduced or mixed into the feed in any manner known in the art. Approximately 0.5 to 1.0 gram of thiamin per head per day is added to the feed. For example, for calves weighing approximately 450 lbs., this amounts to 0.5 to 1.0 gram of thiamin nitrate per 3.2 lbs. of ground corn.

The feeding of the thiamin containing feed to the cattle continues until such time as the cattle have substantially recovered from the tall fescue toxicosis. Research indicates that approximately 60 days treatment may be required for recovery.

Thiamin may also be used to supplement the diet of farm animals such as cattle grazing in endophyte infected fescue fields in order to prevent the adverse effects of tall fescue toxicosis. Specifically, the thiamin may be mixed into mineral supplements or salt blocks in these fields for the cattle. The dosage level sufficient to produce prophylactic effects with respect to tall fescue toxicosis symptoms is approximately 0.000625 to 0.002 grams of thiamin per pound of animal. This is used as a measure in preparing the thiamin supplemented mineral.

The following examples are given to illustrate the invention as it is presently preferred to practice it. It should be understood, however, that these examples are illustrative and the invention is not to be considered as restricted thereto except as indicated in the appended claims.

EXAMPLE 1

A grazing study of 60 crossbred yearling steers was conducted from April to September. The steers grazing on endophyte free fescue (EFF) Kenhy pastures gained on the average 0.93 kg/day while steers grazing on high endophyte fescue (HEF) KY-31 pastures gained on the average 0.49 kg/day. The cattle grazing on HEF exhibited typical summer or tall fescue toxicosis symptoms of reduced performance, elevated rectal temperatures and rough hair coats.

Upon termination of the grazing studies, ten head of these cattle were slaughtered for gross and histological examination of various tissues. The remaining cattle having an average weight of 445 and 349 kg for the EFF and HEF grazing groups, respectively, were assigned to a dry lot experiment where they were fed corn and corn silage with and without a thiamin supplement. The average initial rectal temperature was 39.9° C. and 41.0° C. (P<.01) for the EFF and HEF grazing groups, respectively. After 13 days on thiamin supplemented feed, rectal temperatures for the HEF group had dropped to normal with both the EFF and HEF groups exhibiting substantially identical average temperatures.

Dietary supplementation with 0.5 gm of thiamin per head per day benefited performance in the HEF group by 0.19 kg per day (P<.09). Histological examination of the cerebrum, kidney, heart, skeletal muscle, liver, thyroid, adrenals, spleen, abomasum, small intestine, large intestine and pituitary tissues showed no significant lesions that could be attributed to tall fescue toxicosis. The lungs, however, did reveal bronchiolar pneumonia to varying degrees.

EXAMPLE 2

96 head of weanling calves weighing an average of 451 lbs. were stratified by sex and breed type and allotted to 12 equal groups. As seen from viewing Table 1 below, 24 of the calves were fed endophyte free haylage, 24 of the calves were fed endophyte free haylage supplemented with thiamin, 24 calves were fed high endophyte haylage and the remaining 24 calves were fed high endophyte haylage supplemented with thiamin.

TABLE 1

Performance of Weanling Calves on High Endophyte and Endophyte Free Fescue Haylage with and without Thiamin

| | Haylage Treatments | | | |
|---|---|---|---|---|
| | Endophyte Free | Endophyte Free & Thiamin | High Endophyte | High Endophyte & Thiamin |
| No calves | 24 | 24 | 24 | 24 |
| Avg. begin shrunk wt. lbs. | 449.5 | 458.4 | 452.0 | 450.1 |
| Avg. End | 503.4 | 510.3 | 509.2 | 514.7 |

TABLE 1-continued

Performance of Weanling Calves on
High Endophyte and Endophyte Free
Fescue Haylage with and without Thiamin

| | Haylage Treatments | | | |
|---|---|---|---|---|
| | Endophyte Free | Endophyte Free & Thiamin | High Endophyte | High Endophyte & Thiamin |
| shrunk wt. lbs. | | | | |
| Avg. Daily gain | .77 | .74 | .81 | .92 |
| DDMI. lbs | 10.0 | 9.6 | 9.5 | 9.3 |
| F:G | 13.0 | 13.0 | 11.8 | 10.1 |

Within each haylage group, calves were fed 0, 0.5 or 1.0 grams per head per day of thiamin as thiamin mononitrate in 3.2 lbs. of ground corn. Haylage was fed to appetite. The calves were maintained in drylot with eight head per pen (3×2 replicated) for 70 days. Gains and feed efficiency were calculated on a shrunk basis.

There was no observed response among the endophyte free haylage fed calves to thiamin. On the other hand, thiamin supplementation at either 0.5 or 1.0 grams per head per day provided a 13.6% improvement in daily gains and a 14.4% improvement in feed per unit of gain in the high endophyte haylage fed calves.

We claim:

1. A method of treating and substantially alleviating the symptoms of tall fescue toxicosis in a domestic farm animal, comprising:
orally administering thiamin to said animal suffering from tall fescue toxicosis at therapeutic levels sufficient for treating tall fescue toxicosis of approximately 0.000625 to 0.002 g/lb of the animal per day for approximately 60 days.

2. A method of treating and alleviating the symptoms of tall fescue toxicosis in a domestic farm animal, comprising the steps of:
introducing thiamin into feed for said animal suffering from tall fescue toxicosis at therapeutic levels sufficient for treating tall fescue toxicosis, said levels being between 0.5 and 1.0 gram per day per animal; and
feeding said thiamin containing feed to said animal for approximately 60 days.

3. The method set forth in claim 2, wherein said thiamin is in the form of thiamin nitrate.

4. A method of preventing tall fescue toxicosis in a domestic farm animal grazing or feeding on endophyte infected tall fescue, comprising the steps of:
supplementing the diet of the animal feeding on endophyte infected tall fescue with thiamin at a dosage level of approximately 0.000625 to 0.002 g/lb. of the animal; and dosage level being sufficient to produce prophylactic effects with respect to tall fescue toxicosis symptoms; and
continuing said thiamin supplementation for as long as said animal continues to graze or feed on said endophyte infected tall fescue.

* * * * *